US006849685B2

(12) United States Patent
Soerens et al.

(10) Patent No.: US 6,849,685 B2
(45) Date of Patent: Feb. 1, 2005

(54) METHOD FOR MAKING AN ABSORBENT BINDER COMPOSITION AND APPLICATION THEREOF TO A SUBSTRATE

(75) Inventors: Dave Allen Soerens, Neenah, WI (US); Jason Matthew Laumer, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 167 days.

(21) Appl. No.: 10/324,478

(22) Filed: Dec. 20, 2002

(65) Prior Publication Data

US 2004/0019166 A1 Jan. 29, 2004

Related U.S. Application Data

(63) Continuation-in-part of application No. 10/206,883, filed on Jul. 26, 2002, now Pat. No. 6,737,491.

(51) Int. Cl.$^7$ .............................................. C08L 51/00
(52) U.S. Cl. ....................... 524/539; 524/458; 524/525; 524/528; 524/833; 524/837
(58) Field of Search ................................ 524/458, 525, 524/528, 539, 833, 837

(56) References Cited

U.S. PATENT DOCUMENTS

| | | | |
|---|---|---|---|
| 3,617,362 A | 11/1971 | Bemmels et al. | |
| 3,951,893 A | * 4/1976 | Gander | ........................ 524/322 |
| 3,963,605 A | 6/1976 | Seabourn | |
| 4,251,643 A | 2/1981 | Harada et al. | |
| 4,291,136 A | 9/1981 | Keogh | |
| 4,328,323 A | 5/1982 | Keogh | |
| 4,343,917 A | 8/1982 | Keogh | |
| 4,353,997 A | 10/1982 | Keogh | |
| 4,369,289 A | 1/1983 | Keogh | |
| 4,408,011 A | 10/1983 | Barnabeo | |
| 4,434,272 A | 2/1984 | Keogh | |
| 4,440,907 A | 4/1984 | Keogh | |
| 4,446,279 A | 5/1984 | Keogh | |
| 4,459,396 A | 7/1984 | Yamasaki et al. | |
| 4,489,029 A | 12/1984 | Keogh et al. | |
| 4,493,924 A | 1/1985 | Rifi | |
| 4,526,930 A | 7/1985 | Keogh | |
| 4,551,504 A | 11/1985 | Barnabeo | |
| 4,575,535 A | 3/1986 | Keogh | |
| 4,579,913 A | 4/1986 | Keogh | |
| 4,593,071 A | 6/1986 | Keogh | |
| 4,676,820 A | 6/1987 | Le Sergent et al. | |
| 4,753,993 A | 6/1988 | Keogh | |
| 4,767,820 A | 8/1988 | Keogh | |
| 4,921,136 A | 5/1990 | Roggenburg, Jr. | |
| 4,940,646 A | 7/1990 | Pawlowski | |
| 5,047,476 A | 9/1991 | Keogh | |
| 5,089,564 A | 2/1992 | Bullen | |
| 5,112,919 A | 5/1992 | Furrer et al. | |
| 5,145,906 A | 9/1992 | Chambers et al. | |
| 5,196,470 A | 3/1993 | Anderson et al. | |
| 5,204,404 A | 4/1993 | Werner, Jr. et al. | |
| 5,364,382 A | 11/1994 | Latimer et al. | |
| 5,389,728 A | 2/1995 | Prejean | |
| 5,532,350 A | 7/1996 | Cottrell et al. | |
| 5,656,132 A | 8/1997 | Farrington, Jr. et al. | |
| 5,853,867 A | * 12/1998 | Harada et al. | ........... 428/317.9 |
| 5,859,074 A | 1/1999 | Rezai et al. | |
| 5,911,937 A | 6/1999 | Hekal | |
| 5,932,668 A | 8/1999 | Friebe et al. | |
| 5,961,763 A | 10/1999 | Makoui et al. | |
| 6,020,171 A | 2/2000 | Saito et al. | |
| 6,054,523 A | 4/2000 | Braun et al. | |
| 6,110,533 A | 8/2000 | Coté et al. | |
| 6,300,275 B1 | * 10/2001 | Weir | .......................... 502/402 |
| 6,380,298 B2 | 4/2002 | Flautt et al. | |
| 6,403,857 B1 | 6/2002 | Gross et al. | |
| 6,417,425 B1 | 7/2002 | Whitmore et al. | |
| 6,596,402 B2 | 7/2003 | Soerens et al. | |
| 6,689,934 B2 | * 2/2004 | Dodge et al. | ................ 604/367 |
| 2002/0090453 A1 | 7/2002 | Muthiah et al. | |
| 2003/0149413 A1 | 8/2003 | Mehawej | |

FOREIGN PATENT DOCUMENTS

| | | |
|---|---|---|
| CA | 756190 | 4/1967 |
| EP | 0 132 910 A2 | 2/1985 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 199 059 | 4/2002 |
| WO | 99/57201 | 11/1999 |
| WO | WO 02/053664 A2 | 7/2002 |

* cited by examiner

Primary Examiner—Helen L. Pezzuto
(74) Attorney, Agent, or Firm—Pauley Petersen & Erickson

(57) ABSTRACT

A method of making an absorbent binder composition includes combining a first aqueous monomer solution including a reducing polymerization initiator with a second aqueous monomer solution including an oxidizing polymerization initiator to form a binder composition having post application, moisture-induced crosslinking capability. The first aqueous monomer solution includes a monoethylenically unsaturated monomer and an ethylenically unsaturated monomer that contains an alkoxysilane functionality. The second aqueous monomer solution includes a monoethylenically unsaturated monomer. The monoethylenically unsaturated monomer included in the first and second aqueous monomer solutions may be carboxylic, sulphonic, or phosphoric acids or salts or a combination thereof. The ethylenically unsaturated monomer may be an acrylate or methacrylate. Crosslinking of the resulting binder composition is induced by removal of water. The polymerization of the monomer solutions to form an absorbent binder composition may be carried out in about 100 minutes or less.

30 Claims, No Drawings

METHOD FOR MAKING AN ABSORBENT BINDER COMPOSITION AND APPLICATION THEREOF TO A SUBSTRATE

This application is a continuation-in-part of U.S. patent application Ser. No. 10/206,883 filed Jul. 26, 2002 now U.S. 6,737,491, entitled "Absorbent Binder Composition and Method of Making Same".

BACKGROUND OF THE INVENTION

Adhesives, or binders, are a necessary element of many absorbent products. While adhesives beneficially hold products together, they may also have a tendency to interfere with the absorption of fluid by the absorbent product because they are typically hydrophobic and/or non-absorbent in nature.

Hydrophilic adhesives are known. These adhesives are typically formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have also been used to provide hydrophilic adhesives. These materials provide adhesion under dry conditions. However, upon exposure to aqueous fluids, these materials lose bonding capability because they are substantially soluble in aqueous fluids.

A known approach for making hydrophilic adhesives more functional upon exposure to aqueous fluid is to crosslink water-soluble polymers. As a result of crosslinking, the material becomes swellable, and no longer soluble, in aqueous fluids. However, crosslinked polymers are difficult to apply to substrates or to establish intimate contact with surfaces because the crosslinked polymers are solid materials that have little or no ability to flow.

What therefore is needed is a hydrophilic binder composition or coating that has latent crosslinking capability. Such a binder composition could be easily applied, like a water-soluble polymer, since the hydrophilic binder composition would be capable of flowing prior to crosslinking. Latent crosslinking capability would also provide a simple means of crosslinking the binder composition after it has established intimate contact with a substrate or has formed a desired final shape or form.

One method for making such a binder composition includes a two-step process wherein monoethylenically unsaturated monomers, one of which contains alkoxysilane functionality, are polymerized and the resulting binder composition is then neutralized. The polymerization reaction is generally carried out in an organic solvent such as ethanol. Thereafter, crosslinking of the resulting binder composition can be moisture-induced by hydrolysis and condensation of the alkoxysilane during solvent removal.

Typically, the polymerization process of this method take about 6 to about 8 hours to complete followed by an additional period of time to effectively neutralize the resulting binder composition. Furthermore, this method requires the removal of the organic solvent, which may or may not be recovered.

There is thus a need for a method of making an absorbent binder composition that is faster. There is also a need for a method of making an absorbent binder composition that generates a lower level of organic waste. Furthermore, there is a need for an absorbent binder composition that is less expensive to prepare.

SUMMARY OF THE INVENTION

In response to the difficulties encountered with the two-step polymerization process discussed above, an aqueous-based method of making an absorbent binder composition has been developed that is both faster and less expensive. The method is faster because both the polymerization and the neutralization reactions may be carried out in a single step. The absorbent binder composition is less expensive to prepare by this method because the organic solvents and the need to recover or discard them has been eliminated.

The absorbent binder composition of the invention can be made by combining a first aqueous monomer solution including a reducing polymerization initiator with a second aqueous monomer solution including an oxidizing polymerization initiator wherein the initiators react to form a binder composition. The polymerization of the monomer solutions to form an absorbent binder composition may be carried out in about 100 minutes or less. The first aqueous monomer solution includes a monoethylenically unsaturated monomer such as a carboxylic acid salt, a sulphonic acid salt, a phosphoric acid salt or a combination thereof and an ethylenically unsaturated monomer including an acrylate or a methacrylate that contains an alkoxysilane functionality. The second aqueous monomer solution includes a monoethylenically unsaturated monomer such as a carboxylic acid salt, a sulphonic acid salt, a phosphoric acid salt or a combination thereof. Crosslinking of the resulting binder composition may be induced by concentrating the combined monomer solutions through the removal of water to promote condensation of silanols generated by the hydrolysis of the alkoxysilanes.

In another embodiment, an absorbent binder composition of the invention may be made by combining a first aqueous solution including a reducing polymerization initiator, a monoethylenically unsaturated monomer such as a carboxylic acid, a sulphonic acid, a phosphoric acid or a combination thereof and an ethylenically unsaturated monomer including an acrylate or a methacrylate that contains an alkoxysilane functionality with a second aqueous solution including an oxidizing polymerization initiator and a monoethylenically unsaturated monomer such as a carboxylic acid, a sulphonic acid, a phosphoric acid or a combination thereof. An amount of a basic material effective to at least partially neutralize the monoethylenically unsaturated monomer may be added to the first monomer solution and/or the second monomer solution.

Definitions

"Binder" includes materials that are capable of attaching themselves to a substrate, attaching other substances to a substrate or attaching at least two materials together.

"Feminine hygiene products" include sanitary pads and napkins, as well as tampons and interlabial feminine hygiene products.

"Fluid" refers to a substance in the form of a liquid or gas at room temperature and atmospheric pressure.

"High density polyethylene (HDPE)" refers to a polyethylene having a density of about 0.95 g/cm$^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to 0.935 g/cm$^3$.

"Low density polyethylene (LDPE)" refers to a polyethylene having a density between about 0.91 and about 0.925 g/cm$^3$.

"Monomer(s)" as used herein includes monomers, oligomers, polymers, mixtures of monomers, oligomers and/or polymers, and any other reactive chemical species which are capable of co-polymerization with monoethylenically unsaturated carboxylic, sulphonic or phosphoric acid or salts thereof.

"Modifying agent" refers to a substance that may be added to a composition to modify the physical properties of the composition, such as the color, texture or response to applied forces of the composition.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Personal care product" includes diapers, diaper pants, training pants, swim wear, absorbent underpants, adult incontinence products, feminine hygiene products, and the like.

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Substrate" refers to a material or surface onto which another material may be applied or coated. Such substrates include, but are not limited to, nonwoven, woven, and knitted fabrics; cellulosic tissue sheets; plastic films, including polypropylene, low density polyethylene, high density polyethylene, linear low density polyethylene, and ultra low density polyethylene; LYCRA stranded composites; and elastomer net composites.

"Superabsorbent" refers to a water-swellable, water-insoluble organic or inorganic material capable, under the most favorable conditions, of absorbing at least about 10 times its weight and, more desirably, at least about 20 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as cross-linked polymers.

"Ultra low density polyethylene (ULDPE)" refers to polymers of ethylene and higher alpha-olefin comonomers such as $C_3$–$C_{12}$ comonomers, and combinations thereof, having a density of about 0.860 to less than 0.900 g/cm$^3$.

DESCRIPTION OF PREFERRED EMBODIMENTS

The present invention is directed to a method for making an absorbent binder composition that includes a hydrophilic polymer having the capability of post-application, moisture-induced crosslinking. The method is carried out in a single step wherein polymerization and neutralization of the absorbent binder composition is achieved in about 60 minutes or less. The polymerization/neutralization reaction is conducted in an aqueous medium thereby eliminating the need for organic solvents.

More specifically, the absorbent binder composition is made by combining a first aqueous monomer solution including a reducing polymerization initiator with a second aqueous monomer solution including an oxidizing polymerization initiator, wherein the initiators react to form a binder composition. The first aqueous monomer solution further includes a monoethylenically unsaturated monomer and an ethylenically unsaturated monomer that contains an alkoxysilane functionality. The second aqueous monomer solution includes a monoethylenically unsaturated monomer. Suitably, the binder composition is formed in about 100 minutes or less, or 60 minutes or less, desirably in about 30 minutes or less, or about 15 minutes or less, and in one embodiment about 10 minutes or less. The binder composition is subsequently applied to a substrate and crosslinking of the binder composition is induced by concentrating the combined monomer solutions through the removal of water to promote condensation of silanols generated by the hydrolysis of the alkoxysilanes.

Suitable monoethylenically unsaturated monomers that may be included in the first and the second aqueous monomer solutions include carboxyl group-containing monomers: monoethylenically unsaturated mono or poly-carboxylic acids, such as (meth)acrylic acid (meaning acrylic acid or methacrylic acid; similar notations are used hereinafter), maleic acid, fumaric acid, crotonic acid, sorbic acid, itaconic acid, and cinnamic acid;

Carboxylic acid anhydride group-containing monomers: monoethylenically unsaturated polycarboxylic acid anhydrides (such as maleic anhydride);

Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

Sulfonic acid group-containing monomers: aliphatic or aromatic vinyl sulfonic acids (such as vinyl sulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propylsulfonic acid];

Sulfonic acid salt group-containing monomers: alkali metal salts, ammonium salts, amine salts of sulfonic acid group containing monomers as mentioned above; and/or Amide group-containing monomers: vinylformamide, (meth)acrylamide, N-alkyl (meth)acrylamides (such as N-methylacrylamide, N-hexylacrylamide), N,N-dialkyl (meth)acrylamides (such as N,N-dimethylacrylamide, N,N-di-n-propylacrylamide), N-hydroxalkyl (meth)acrylamides [such as N-methylol(meth)acrylamide, N-hydroxyethyl (meth)acrylamide], N,N-dihydroxyalkyl(meth)acrylamides [such as N,N-dihydroxyethyl (meth)acrylamide], vinyl lactams (such as N-vinylpyrrolidone).

In one embodiment, the first and/or second aqueous monomer solution may include a monoethylenically unsaturated monomer such as a carboxylic acid salt, a sulphonic acid salt, a phosphoric acid salt or a combination thereof.

In another embodiment, the first and/or the second aqueous solution may include a monoethylenically unsaturated monomer such as a carboxylic acid, a sulphonic acid, a phosphoric acid or a combination thereof that may be at least partially neutralized or converted to the salt form in situ. In this embodiment, an amount of a basic material, such as sodium hydroxide, effective to at least partially neutralize the monoethylenically unsaturated monomer may be included in the first and/or second aqueous solution. Alternatively, the monoethylenically unsaturated monomer may be added to a basic solution such as, for example, a sodium hydroxide solution to form an aqueous monomer solution. Desirably, the monoethylenically unsaturated monomer in the first and/or second aqueous monomer solution is neutralized to provide a solution pH of about 5 to about 8 prior to polymerization with the ethylenically unsaturated monomer. One monoethylenically unsaturated monomer suitable for use in this embodiment includes acrylic acid.

Suitably, the pH of the first and/or second aqueous monomer solution is adjusted to about 6.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 6.5 to about 7.0.

The first and second aqueous monomer solutions may include the monoethylenically unsaturated monomer in any suitable proportion to form an absorbent binder composition including about 15 to about 99.9 composition weight percent monoethylenically unsaturated carboxylic, sulphonic or phosphoric acid or salts thereof. Typically, the levels of monoethylenically unsaturated carboxylic, sulphonic or phosphoric acid or salts thereof in the absorbent binder composition may be between about 25 and about 90 composition weight percent; particularly between about 30 and about 80 composition weight percent; or between about 50 and about 70 composition weight percent for some intended uses.

The first aqueous monomer solution also includes an organic monomer capable of co-polymerization with monoethylenically unsaturated carboxylic, sulphonic or phosphoric acid or salts thereof. Organic monomers that contain a trialkoxy silane functional group or a moiety that reacts with water to form a silanol group, are useful in the practice of this invention. The trialkoxy silane functional group has the following structure:

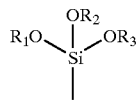

wherein $R_1$, $R_2$ and $R_3$ are alkyl groups independently having from 1 to 6 carbon atoms. Ethylenically unsaturated monomers containing a trialkoxy silane functional group are appropriate for this invention and are desired. Desired ethylenically unsaturated monomers include acrylates and methacrylates. A suitable ethylenically unsaturated monomer containing a trialkoxy silane functional group is 3-(trimethoxysilyl)propyl methacrylate. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects and are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The first aqueous monomer solution may include the ethylenically unsaturated monomer containing a trialkoxy silane functional group in any suitable proportion to provide an absorbent binder composition including about 0.1 to about 20 composition weight percent ethylenically unsaturated monomer. Suitably, the amount of ethylenically unsaturated monomer containing a trialkoxy silane functional group should exceed 0.1 composition weight percent in order to provide sufficient crosslinking upon removal of water. Typically, the monomer addition levels are between about 0.1 and about 15 composition weight percent; particularly, between about 1.0 and about 10 composition weight percent; or between about 1.5 and about 5.5 composition weight percent for some intended uses.

In one embodiment, a surfactant may be added to the first and/or second aqueous monomer solution to disperse the ethylenically unsaturated monomer. One surfactant suitable for use in the present invention is a dioctyl sodium sulfosuccinate available under the trademark AEROSOL OT from Cytec Industries, Inc. of Paterson, N.J.

The first aqueous monomer solution further includes a reducing polymerization initiator. Suitable reducing polymerization initiators include, but are not limited to, ascorbic acid, alkali metalsulfites, alkali metal bisulfites, ammonium sulfite, ammonium bisulfite, alkali metalhydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form a binder composition including a monoethylenically unsaturated monomer and an ethylenically unsaturated monomer that has post-application, moisture-induced crosslinking capability.

The binder composition may be applied to a substrate and subsequently dried to form a cast film. Once the binder composition is applied to the substrate, crosslinking can be moisture-induced by hydrolysis and condensation of alkoxysilanes. For example, crosslinking of the binder composition can be induced by concentrating the binder composition on the substrate through the removal of the water to promote condensation of silanols generated by hydrolysis of alkoxysilanes. Typically, crosslinking begins at a solution concentration above about 30 percent by weight binder composition.

Alternatively, the resulting binder composition may be applied to a substrate, such as for the purpose of adhering various components of an absorbent product to one another during the manufacturing process of absorbent products. In another embodiment, the binder composition may be applied to a substrate as a coating by itself, thereby serving as an absorbency additive. In either of these embodiments, the binder composition is suitably present in any concentration that provides a viscosity suitable for the application process. The binder composition may be applied to the substrate using any suitable application process, including knife over roll coating, or roll coating, either in a continuous coverage or a patterned coverage. Printing applications are other suitable application techniques, including gravure printing, screen, and jet printing. The binder composition may also be applied to the substrate using a spray application.

In another embodiment, the absorbent binder composition may be prepared using a continuous process wherein the polymerization and/or neutralization reaction is carried out in a suitable reactor that conveys the resulting binder composition, upon completion of the polymerization reaction, directly to an apparatus for applying the absorbent binder composition onto the substrate. Such a continuous process may be desirable where conditions, such as high heat, may cause premature crosslinking of the binder composition that would hinder application of the absorbent binder composition onto the substrate.

For some intended uses the absorbent binder composition of this invention provides very flexible coatings and should therefore have a glass transition temperature about 30 degrees Celsius or below, or about 10 degrees Celsius or below, as measured by Differential Scanning Calorimetry (DSC), and a bending modulus lower than the substrate to which they are applied. Suitably, the absorbent binder composition, in combination with the substrate, has a Gurley stiffness value about 320 milligrams (mg) or less, or about 160 mg or less, or about 60 mg or less. Suitable substrates to which the binder composition may be applied include, but are not limited to, nonwoven, woven, and knitted fabrics; cellulosic tissue sheets; plastic films, including polypropylene, low density polyethylene, high density polyethylene, linear low density polyethylene, and ultra low density polyethylene; LYCRA stranded composites; and elastomer net composites.

Furthermore, crosslinked films of the absorbent binder composition are capable of absorbing about 80 percent or more of their dry weight of 0.9% saline solution with no load applied during swelling. The absorbency of absorbent binder composition may range from about 80 percent to about 4000 percent of its dry weight of 0.9% saline solution with no load applied during swelling. Typical absorbency with no load applied during swelling is from about 80 to about 1500 percent of dry weight, particularly, between about 100 and about 900 percent; or between about 300 and about 700 percent of dry weight for some intended uses.

The absorbent binder composition can be used in the manufacture of absorbent products, thereby adding absorbent capacity to such absorbent products. Examples of such articles include training pants, diapers, diaper pants, feminine hygiene products, swimwear, incontinence products, absorbent toweling, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults.

EXAMPLE

A first aqueous monomer solution was prepared as follows. First, 21.0 grams (0.53 moles) of sodium hydroxide was dissolved in 138.4 grams of deionized water. The resulting sodium hydroxide solution was cooled with an ice bath to room temperature. Then, a neutralized acrylic acid solution was formed by adding 48 milliliters (0.70 moles) of acrylic acid to the cooled sodium hydroxide solution. Thereafter, a total of 68 grams of 10% (w/w) sodium hydroxide solution was added to the neutralized acrylic acid solution to adjust the pH to 6.8. Next, 0.6215 grams ($3.53 \times 10^{-3}$ moles) of ascorbic acid was dissolved in the neutralized acrylic acid solution. Following dissolution of the ascorbic acid, 0.55 milliliters (0.6 grams) of AEROSOL OT surfactant was added to the solution and the solution was placed on a hot plate and heated to about 40 degrees Celsius to fully dissolve the surfactant. Finally, 2.6 milliliters ($1.41 \times 10^{-2}$ moles) of 3-(trimethoxysilyl)propyl methacrylate was added to the solution to form a first aqueous monomer solution. The first aqueous monomer solution was hazy indicating fine dispersion of the 3-(trimethoxysilyl)propyl methacrylate.

A second aqueous monomer solution was prepared as follows. First, 21.0 grams (0.53 moles) of sodium hydroxide was dissolved in 138.4 grams of deionized water. The resulting sodium hydroxide solution was cooled with an ice bath to room temperature. Then, a neutralized acrylic acid solution was formed by adding 48 milliliters (0.70 moles) of acrylic acid to the cooled sodium hydroxide solution. Thereafter, a total of 68 grams of 10% (w/w) sodium hydroxide solution was added to the neutralized acrylic acid solution to adjust the pH to 6.8. Finally, 1.8 milliliters ($1.76 \times 10^{-2}$ moles) of 30% (w/w) hydrogen peroxide solution in water was added to the neutralized acrylic acid solution to form a second aqueous monomer solution.

The second aqueous monomer solution was added to the first aqueous monomer solution to form a polymerization solution. The polymerization solution was stirred with a magnetic stir bar. Upon combining the first and second monomer solutions, the polymerization reaction began. A maximum polymerization temperature of about 60 degrees Celsius was noted approximately 5 minutes after combining the monomer solutions. Total reaction time was approximately 10 minutes.

After the completion of the polymerization reaction, the resulting aqueous binder solution was used to cast a binder film by pouring 22.6 grams of the solution into a polystyrene weigh boat having a surface area of about 100 centimeters and allowing the water to evaporate overnight in a fume hood. The binder film was further dried for about 50 minutes at a temperature of 50 degrees Celsius. The resulting binder film weighed 5.95 grams, indicating a solution concentration of about 26 weight percent binder composition.

A 0.4-gram sample was cut from the binder film and placed in about 20 grams of 0.9% saline solution. After soaking for about 60 minutes the swollen film sample was removed from the saline solution, blotted with a paper towel to remove surface moisture and weighed. The swollen film sample had a weight of 4.4 grams indicating an absorbency with no load of about 1000 percent of its dry weight of 0.9% saline.

Test Method for Determining Stiffness

A suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-E manufactured by Teledyne Gurley, a business having offices in Troy, N.Y. For purposes of the present invention, the stated Gurley stiffness values are intended to correspond to the values that would be generated by a "standard" sized sample. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

Test Method for Determining Absorbent Capacity

Centrifuge Retention Capacity: As used herein, the Centrifugal Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9% saline solution) to be freely absorbed by the sample. A heat-sealable tea bag material (available from Dexter Nonwovens of Windsor Locks, Conn., U.S.A., as item #11697) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5-inch). Three sample bags are tested for each material.

The sealed bags are submerged in a pan of 0.9 percent NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at a target of 1600 rpm, but within the range of 1500–1900 rpm, for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. A method of making an absorbent binder composition comprising:
   forming a first aqueous monomer solution including a monoethylenically unsaturated monomer selected from the group consisting of carboxylic acid salts, sulphonic acid salts, phosphoric acid salts, and combinations thereof; an ethylenically unsaturated monomer including an acrylate or a methacrylate that contains an alkoxysilane functionality; and a reducing polymerization initiator;
   forming a second aqueous monomer solution including a monoethylenically unsaturated monomer selected from the group consisting of carboxylic acid salts, sulphonic acid salts, phosphoric acid salts, and combinations thereof; and an oxidizing polymerization initiator;
   combining the first aqueous monomer solution with the second aqueous monomer solution wherein the reducing polymerization initiator reacts with the oxidizing polymerization initiator to form a binder composition; and
   inducing crosslinking of the binder composition by removal of water.

2. The method of claim 1, wherein the binder composition is formed in about 100 minutes or less.

3. The method of claim 1, wherein the binder composition is formed in about 30 minutes or less.

4. The method of claim 1, wherein the binder composition is formed in about 15 minutes or less.

5. The method of claim 1, wherein the binder composition is formed in about 10 minutes or less.

6. The method of claim 1, further comprising applying the binder composition to a substrate prior to inducing crosslinking of the binder composition by the removal of water.

7. The method of claim 1, further comprising adjusting the first aqueous monomer solution to have a pH of about 6.5 to about 7.

8. The method of claim 1, further comprising adjusting the second aqueous monomer solution to have a pH of about 6.5 to about 7.

9. The method of claim 1, wherein the reducing polymerization initiator is selected from the group consisting of ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof.

10. The method of claim 1, wherein the oxidizing polymerization initiator is selected from the group consisting of hydrogen peroxide, alkali metal persulfates, ammonium persulfate, alkylhydroperoxides, peresters, diacryl peroxides, silver salts, and combinations thereof.

11. A method of making an absorbent binder composition comprising:

forming a first aqueous monomer solution including a monoethylenically unsaturated monomer selected from the group consisting of carboxylic acids, sulphonic acids, phosphoric acids, and combinations thereof; an ethylenically unsaturated monomer including an acrylate or a methacrylate that contains an alkoxysilane functionality; and a reducing polymerization initiator;

forming a second aqueous monomer solution including a monoethylenically unsaturated monomer selected from the group consisting of carboxylic acids, sulphonic acids, phosphoric acids, and combinations thereof; and an oxidizing polymerization initiator;

combining the first aqueous monomer solution with the second aqueous monomer solution wherein the reducing polymerization initiator reacts with the oxidizing polymerization initiator to form a binder composition; and inducing crosslinking of the binder composition by removal of water.

12. The method of claim 11, wherein the binder composition is formed in about 100 minutes or less.

13. The method of claim 11, wherein the first aqueous monomer solution comprises a basic material in an amount effective to at least partially neutralize the monoethylenically unsaturated monomer.

14. The method of claim 11, wherein the second aqueous monomer solution comprises a basic material in an amount effective to at least partially neutralize the monoethylenically unsaturated monomer.

15. The method of claim 11, further comprising adding a surfactant to the first aqueous monomer solution to disperse the ethylenically unsaturated monomer.

16. The method of claim 11, further comprising adding a surfactant to the second aqueous monomer solution.

17. The method of claim 11, further comprising applying the binder composition to a substrate prior to inducing crosslinking of the binder composition by the removal of water.

18. A method for making an absorbent binder composition comprising:

forming a first aqueous monomer solution including a monoethylenically unsaturated monomer selected from the group consisting of carboxylic acids, sulphonic acids, phosphoric acids, and combinations thereof; and an ethylenically unsaturated monomer including an acrylate or a methacrylate that contains an alkoxysilane functionality;

adding an amount of a basic material to the first aqueous monomer solution effective to neutralize the monoethylenically unsaturated monomer;

adjusting the first aqueous monomer solution to have a pH of about 6.5 to about 7.0;

adding a reducing polymerization initiator including ascorbic acid to the first aqueous monomer solution;

forming a second aqueous monomer solution including a monoethylenically unsaturated monomer selected from the group consisting of carboxylic acids, sulphonic acids, phosphoric acids, and combinations thereof;

adding an amount of a basic material to the second aqueous monomer solution effective to neutralize the monoethylenically unsaturated monomer;

adjusting the second aqueous monomer solution to have a pH of about 6.5 to about 7.0;

adding an oxidizing polymerization initiator including hydrogen peroxide to the second aqueous monomer solution;

combining the first aqueous monomer solution with the second aqueous monomer solution wherein the reducing polymerization initiator reacts with the oxidizing polymerization initiator to form a binder composition in about 60 minute or less;

applying the binder composition to a substrate; and inducing crosslinking of the binder composition by removal of water.

19. The method of claim 18, wherein the binder composition is formed in about 30 minutes or less.

20. The method of claim 18, wherein the first aqueous monomer solution comprises acrylic acid and 3-(trimethoxysilyl)propyl methacrylate.

21. The method of claim 18, wherein the second aqueous monomer solution comprises acrylic acid.

22. An absorbent binder composition prepared by the method of claim 1.

23. The absorbent binder composition of claim 22, wherein the absorbent binder composition has a glass transition temperature of about 30 degrees Celsius or lower.

24. The absorbent binder composition of claim 22, wherein the absorbent binder composition has a Centrifugal Retention Capacity of about 80 percent or greater of its dry weight of 0.9% saline.

25. An absorbent binder composition prepared by the method of claim 11.

26. The absorbent binder composition of claim 25, wherein the absorbent binder composition has a glass transition temperature of about 30 degrees Celsius or lower.

27. The absorbent binder composition of claim 25, wherein the absorbent binder composition has a Centrifugal Retention Capacity of about 80 percent or greater of its dry weight of 0.9% saline.

28. An absorbent binder composition prepared by the method of claim 18.

29. The absorbent binder composition of claim 28, wherein the absorbent binder composition has a glass transition temperature of about 30 degrees Celsius or lower.

30. The absorbent binder composition of claim 28, wherein the absorbent binder composition has a Centrifugal Retention Capacity of about 80 percent or greater of its dry weight of 0.9% saline.

* * * * *